United States Patent
Ito et al.

(10) Patent No.: US 7,919,637 B2
(45) Date of Patent: Apr. 5, 2011

(54) FLUORINE-CONTAINING SPIROACETAL COMPOUND AND METHOD OF PRODUCING THE SAME

(75) Inventors: Takayuki Ito, Minami-ashigara (JP); Toshimitsu Sakuma, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 548 days.

(21) Appl. No.: 12/089,593

(22) PCT Filed: Oct. 10, 2006

(86) PCT No.: PCT/JP2006/320516
§ 371 (c)(1),
(2), (4) Date: Apr. 8, 2008

(87) PCT Pub. No.: WO2007/043672
PCT Pub. Date: Apr. 19, 2007

(65) Prior Publication Data
US 2009/0149664 A1    Jun. 11, 2009

(30) Foreign Application Priority Data
Oct. 11, 2005  (JP) .................. 2005-296817

(51) Int. Cl.
*C07D 317/72* (2006.01)
(52) U.S. Cl. .................................... 549/335
(58) Field of Classification Search ............ 549/335
See application file for complete search history.

(56) References Cited

U.S. PATENT DOCUMENTS

| | | | |
|---|---|---|---|
| 3,978,030 A | 8/1976 | Resnick | |
| 4,304,767 A | 12/1981 | Heller et al. | |
| 4,399,264 A | 8/1983 | Squire | |
| 2003/0135067 A1 | 7/2003 | Okazoe et al. | |

FOREIGN PATENT DOCUMENTS

| | | | |
|---|---|---|---|
| JP | 59-078193 A | 5/1984 | |
| JP | 60-142990 A | 7/1985 | |
| JP | 63-295630 A | 12/1988 | |
| JP | 5-70522 A | 3/1993 | |
| WO | WO-02/04397 A1 | 1/2002 | |
| WO | WO-03/037838 A1 | 5/2003 | |
| WO | WO-03/099907 A1 | 12/2003 | |

OTHER PUBLICATIONS 99e-h & Boesken, J et al., Chemical abstracts, 1929, vol. 23, the abstract No. 733.
Moldavskii, D.D. et al., Zhurnal Obshchei Khimii, 1996, 66(12), pp. 1995-2002.
Mirela Balog et al., Tetrahedron, 2004, vol. 60, Issue 22, pp. 4789-4799.

*Primary Examiner* — Janet L. Andres
*Assistant Examiner* — Raymond Covington
(74) *Attorney, Agent, or Firm* — Birch, Stewart, Kolasch & Birch, LLP

(57) ABSTRACT

A fluorine-containing spiroacetal compound represented by the following formula (A):

(A)

[Chemical structure: spiroacetal ring system with F substituents and X groups]

wherein X represents >C(CF$_3$)(Y) or >C=CF$_2$, in which Y represents —CF$_2$OCOR$^1$, —COOR$^2$, —COF, or —CH$_2$OR$^3$, R$^1$ represents an alkyl or cycloalkyl group having at least one fluorine atom, R$^2$ represents a hydrogen atom, an alkali metal, an alkaline earth metal, an alkyl group, or a cycloalkyl group and R$^3$ represents a hydrogen atom or an acyl group; wherein the alkyl or cycloalkyl group for R$^1$ may have a substituent other than fluorine atom; the alkyl or cycloalkyl group for R$^2$ may have a substituent; and the acyl group for R$^3$ may have a substituent.

16 Claims, No Drawings

FLUORINE-CONTAINING SPIROACETAL COMPOUND AND METHOD OF PRODUCING THE SAME

TECHNICAL FIELD

The present invention relates to a difunctional fluorine-containing spiroacetal compound that may be used as a raw material monomer for a fluorine-containing polymer having the characteristics, such as chemical resistance, weather fastness, water/oil repellency, less intermolecular interaction, low refractive index, and high light transmittance. The present invention also relates to a method of producing the compound.

BACKGROUND ART

It is a known fact that difunctional ester compounds, acid halides, and alcohol compounds are useful as monomer components for preparing condensation polymers. Much attention has been recently focused on the characteristics of fluorine compounds, such as chemical resistance, weather fastness, water/oil repellency, less intermolecular interaction, low refractive index, and high light transmittance, and thus development of fluorine-containing polymers has been enthusiastically promoted.

For instance, examples of polycondensation type fluorine-containing polymers for optical waveguide are described in WO03/099907A1 and the references cited therein. It is also described in WO03/037838 A1, JP-A-5-70522 ("JP-A" means unexamined published Japanese patent application), and the references cited therein that polymers obtained by cyclization polymerization of fluorine-containing m-alkenyl vinyl ethers are useful for optical materials such as optical fibers. In addition, it is known that homopolymers of a perfluorodioxol compound as described in U.S. Pat. Nos. 3,978,030 and 4,399,264 and copolymers of this perfluorodioxol compound and tetrafluoroethylene or the like form amorphous polymers, and these can be used in the same applications.

On the other hand, fluorine-containing difunctional compounds and producing methods thereof are described, for example, in WO02/004397.

However, none of the above references describes the fluorine-containing spiroacetal compound of the present invention and producing methods thereof.

DISCLOSURE OF INVENTION

The present inventors studied structures and properties of conventional polymers and found that introduction of a ring structure and an ether bond into the main chain of a polymer imparts the polymer properties, such as being amorphous and a high glass transition temperature (Tg). As a result of further studies, the present inventors have arrived at development of a spiro ring compound having ether bonds (acetal bonds) in its ring structure portion.

The present invention provides:

(1) A fluorine-containing spiroacetal compound represented by the following formula (A):

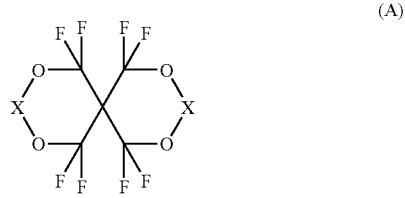

(A)

wherein X represents $>C(CF_3)(Y)$ or $>C=CF_2$, in which Y represents $-CF_2OCOR^1$, $-COOR^2$, $-COF$, or $-CH_2OR^3$, $R^1$ represents an alkyl or cycloalkyl group having at least one fluorine atom, $R^2$ represents a hydrogen atom, an alkali metal, an alkaline earth metal, an alkyl group, or a cycloalkyl group, and $R^3$ represents a hydrogen atom or an acyl group; wherein the alkyl or cycloalkyl group for $R^1$ may have a substituent other than fluorine atom; the alkyl or cycloalkyl group for $R^2$ may have a substituent; and the acyl group for $R^3$ may have a substituent.

(2) The fluorine-containing spiroacetal compound as recited in (1), wherein the compound represented by formula (A) is a compound represented by any one of the following formulae (I), (II), (III), and (IV):

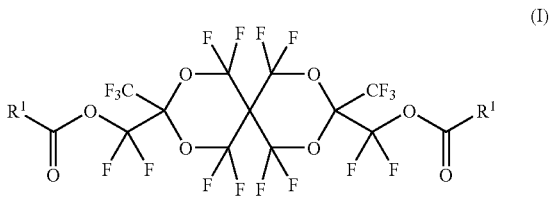

(I)

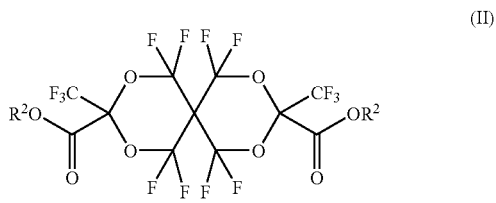

(II)

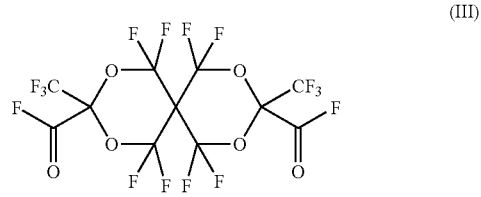

(III)

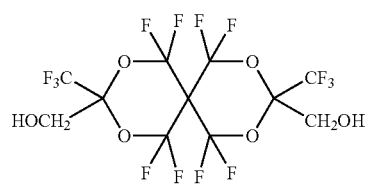

(IV)

wherein $R^1$ represents an alkyl or cycloalkyl group having at least one fluorine atom; $R^2$ represents a hydrogen atom, an alkali metal, an alkaline earth metal, an alkyl group, or a cycloalkyl group; wherein the alkyl or cycloalkyl group for $R^1$ may have a substituent other than fluorine atom, and the alkyl or cycloalkyl group for $R^2$ may have a substituent.

(3) The fluorine-containing spiroacetal compound as recited in (1) or (2), wherein $R^1$ represents a perfluoroalkyl group.

(4) The fluorine-containing spiroacetal compound as recited in (1) or (2), wherein, in formula (A), $R^3$ represents a hydrogen atom or $-COC(R^4)=CH_2$, in which $R^4$ represents a hydrogen atom, a fluorine atom, a methyl group, or a trifluoromethyl group.

(5) A perfluoroester compound represented by formula (I-1).

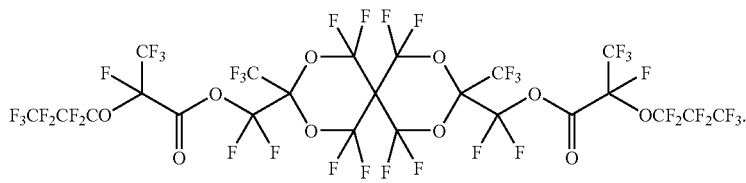

(I-1)

(6) A methylester compound represented by formula (II-1).

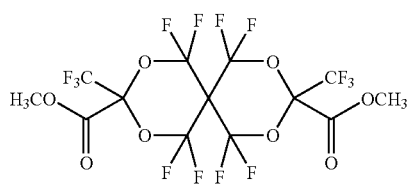

(II-1)

(7) A perfluorodiene compound represented by formula (V).

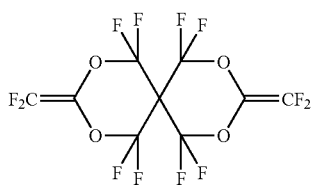

(V)

(8) A fluorine-containing diacrylate compound represented by formula (VI):

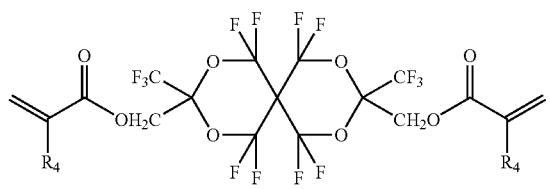

(VI)

wherein $R^4$ represents a hydrogen atom, a fluorine atom, a methyl group, or a trifluoromethyl group.

(9) A method of producing a fluorine-containing spiroacetal compound represented by the following formula (A), which comprises the step of fluorinating a spiroacetal compound obtained by reacting an acyloxyacetone or a pyruvate with a pentaerythritol;

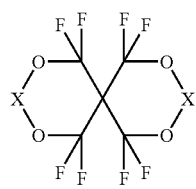

(A)

wherein X represents $>C(CF_3)(Y)$ or $>C=CF_2$, in which Y represents —$CF_2OCOR^1$, —$COOR^2$, —COF, or —$CH_2OR^3$, $R^1$ represents an alkyl or cycloalkyl group having at least one fluorine atom, $R^2$ represents a hydrogen atom, an alkali metal, an alkaline earth metal, an alkyl group, or a cycloalkyl group, and $R^3$ represents a hydrogen atom or an acyl group; wherein the alkyl or cycloalkyl group for $R^1$ may have a substituent other than fluorine atom; the alkyl or cycloalkyl group for $R^2$ may have a substituent; and the acyl group for $R^3$ may have a substituent.

(10) A method of producing a fluorine-containing spiroacetal compound represented by the aforementioned formula (A), which comprises the step of fluorinating a spiroacetal compound obtained by reacting an acyloxyacetone with a pentaerythritol.

(11) The method as recited in (9) or (10), wherein the fluorine-containing spiroacetal compound represented by the aforementioned formula (A) is the compound recited in any one of the above (2) to (8).

The present invention provides a novel difunctional fluorine-containing spiroacetal compound that can be produced from less expensive materials without employing complicated procedures and that gives, by polymerization thereof, a polymer that exhibits excellent performances (performances such as chemical resistance, weather resistance, water and oil repellency, low intermolecular interaction, low refractive index, high light transmittance). Further, the present invention provides a method of producing the aforementioned difunctional fluorine-containing spiroacetal compound.

Other and further features and advantages of the invention will appear more fully from the following description.

BEST MODE FOR CARRYING OUT INVENTION

The compound of the present invention will be explained in detail hereinafter.

In formula (A) according to the present invention, X represents $>C(CF_3)(Y)$ or $>C=CF_2$. Herein, Y represents —$CF_2OCOR^1$, —$COOR^2$, —COF, or —$CH_2OR^3$, in which $R^1$ represents an alkyl or cycloalkyl group having at least one fluorine atom, $R^2$ represents a hydrogen atom, an alkali metal, an alkaline earth metal, an alkyl group, or a cycloalkyl group, and $R^3$ represents a hydrogen atom or an acyl group.

The above alkyl group for $R^1$ preferably has 1 to 20 carbon atoms, more preferably 2 to 10 carbon atoms, and may be linear or branched and, further, it may have a substituent.

The above cycloalkyl group for $R^1$ preferably has 3 to 20 carbon atoms, more preferably 5 to 10 carbon atoms, and, further it may have a substituent. $R^1$ is preferably the above alkyl group.

Examples of the substituent on the above alkyl or cycloalkyl group include substituents to be explained later with regard to $R^2$, in addition to the fluorine atom(s). In particular, the above alkyl group may have an ether bond; and when an alkyl group is substituted on the cycloalkyl group, the alkyl group may have an ether bond. As the alkyl group having an ether bond, an alkyl group substituted with an alkoxy, alkenoxy, cycloalkoxy, or aryloxy group can be mentioned.

R¹ is preferably a perfluoroalkyl group or a perfluorocycloalkyl group, more preferably a perfluoroalkyl group. Specific examples include perfluoromethyl, perfluoroethyl, perfluoropropyl, perfluoroisopropyl, perfluorobutyl, perfluoropentyl, perfluorohexyl, perfluoro(1-methyl-2-oxapentyl), perfluoro(1,4-dimethyl-2,5-dioxaoctyl), perfluorocyclohexyl, perfluoroheptyl, perfluorooctyl, perfluorodecyl, perfluoroundecyl, and perfluorododecyl. The present invention is not limited to these examples.

In formula (A), $R^2$ represents a hydrogen atom, an alkali metal, an alkaline earth metal, an alkyl group, or a cycloalkyl group. The alkyl group for $R^2$ preferably has 1 to 20 carbon atoms, and more preferably 1 to 10 carbon atoms, and may be linear or branched, and it may have a substituent. The cycloalkyl group for $R^2$ preferably has 3 to 20 carbon atoms, and more preferably 5 to 10 carbon atoms, and may have a substituent. Examples of the alkyl and cycloalkyl groups for $R^2$ include methyl, ethyl, propyl, isopropyl, butyl, pentyl, cyclopentyl, hexyl, cyclohexyl, octyl, and decyl. These alkyl and cycloalkyl groups may have a substituent.

Examples of the substituent, which the alkyl group or cycloalkyl group for $R^2$ may have, include halogen atoms (for example, fluorine atom, chlorine atom, bromine atom, and iodine atom), alkyl groups having 20 or less carbon atoms (for example, methyl and ethyl), alkenyl groups having 20 or less carbon atoms (for example, vinyl and allyl), cycloalkyl groups having 20 or less carbon atoms (for example, cyclopentyl, cyclohexyl), cycloalkenyl groups having 20 or less carbon atoms (for example, cyclohexenyl), aryl groups having 30 or less carbon atoms (for example, phenyl and naphthyl), cyano groups, carboxyl groups, alkoxycarbonyl groups having 20 or less carbon atoms (for example, methoxycarbonyl), aryloxycarbonyl groups having 30 or less carbon atoms (for example, phenoxycarbonyl), carbamoyl groups (for example, carbamoyl, N-phenylcarbamoyl, and N,N-dimethylcarbamoyl), alkylcarbonyl groups having 20 or less carbon atoms (for example, acetyl), arylcarbonyl groups having 30 or less carbon atoms (for example, benzoyl), nitro groups, amino groups (for example, amino, dimethylamino, anilino), acylamino groups having 20 or less carbon atoms (for example, acetamido and ethoxycarbonylamino), sulfonamido groups (for example, methanesulfonamido), imido groups (for example, succinimido and phthalimido), imino groups (for example, benzylideneamino), hydroxy groups, alkoxy groups having 20 or less carbon atoms (for example, methoxy), aryloxy groups having 30 or less carbon atoms (for example, phenoxy), acyloxy groups having 20 or less carbon atoms (for example, acetoxy), alkylsulfonyloxy groups having 20 or less carbon atoms (for example, methanesulfonyloxy), arylsulfonyloxy groups having 30 or less carbon atoms (for example, benzenesulfonyloxy), sulfo groups, sulfamoyl groups (for example, sulfamoyl and N-phenylsulfamoyl), alkylthio groups having 20 or less carbon atoms (for example, methylthio), arylthio groups having 30 or less carbon atoms (for example, phenylthio), alkylsulfonyl groups having 20 or less carbon atoms (for example, methanesulfonyl), arylsulfonyl groups having 30 or less carbon atoms (for example, benzenesulfonyl), and heterocyclic groups. The substituent may be further substituted. When plural substituents are present, they may be the same or different. Also, these substituents may be combined with each other to form a ring. Moreover, alkyl groups in the substituent may form an unsaturated bond at a desired position.

Of the alkyl and cycloalkyl groups represented by $R^2$, the alkyl group is preferred. Of these, a methyl group and an ethyl group are more preferred, and a methyl group is particularly preferred.

Examples of the alkali metal and alkaline earth metal represented by $R^2$ include lithium, sodium, potassium, rubidium, cesium, magnesium, calcium, strontium, and barium. Sodium and potassium are preferred, and potassium is more preferred.

In formula (A), $R^3$ represents a hydrogen atom or an acyl group. The acyl group is preferably an acyl group having 1 to 20 carbon atoms (e.g., formyl, acetyl, butylyl, stearoyl, benzoyl, cyclohexanoyl, acryloyl, methacryloyl, isocrotonoyl, and oleyl), and the acyl group may have a substituent. Examples of this substituent include those explained with regard to the above $R^2$. The above acyl group is preferably an alkenoyl group (preferably an alkenoyl group having a vinyl terminal) or a hydroxyalkanoyl group, more preferably an alkenoyl group having a vinyl terminal, still more preferably an acryloyl or methacryloyl that may have a substituent, most preferably —CO($R^4$)=CH$_2$, in which $R^4$ represents a hydrogen atom, a methyl group, or a trifluoromethyl group. $R^4$ is preferably a hydrogen atom or a methyl group, more preferably a hydrogen atom.

The compound represented by formula (A) is preferably a compound represented by any one of the above formulae (I), (II), (III), and (IV), or a compound represented by the above formula (V), or a compound represented by the above formula (VI). Groups in these compounds are the same as the corresponding groups explained with regard to formula (A), and preferred ranges thereof are also as explained with regard to formula (A).

The compound represented by formula (I) is preferably a compound represented by the above formula (I-1), and the compound represented by formula (II) is preferably a compound represented by the above formula (II-1).

Specific examples of the compound represented by formula (A) will be shown below, while this invention shall not be limited by these compounds.

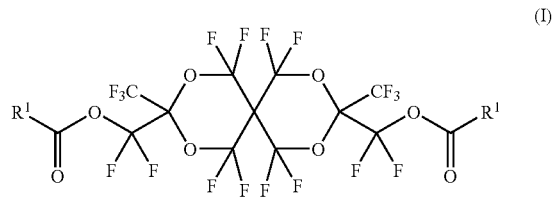

(I)

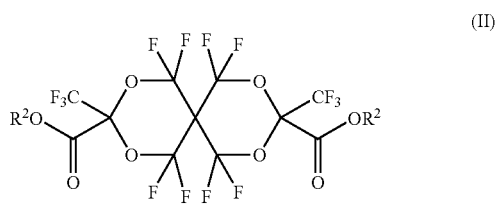

(II)

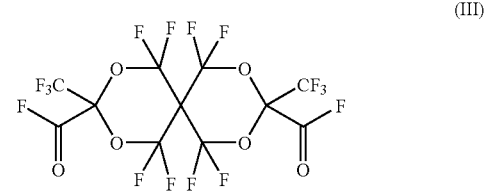

(III)

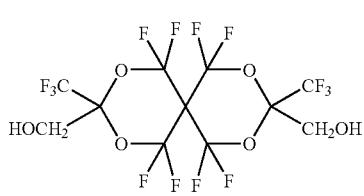

(IV)

(I-1) $R^1$=CF(CF$_3$)OCF$_2$CF$_2$CF$_3$
(I-2) $R^1$=perfluoromethyl
(I-3) $R^1$=perfluoroethyl
(I-4) $R^1$=perfluoropropyl
(I-5) $R^1$=perfluoroisopropyl
(I-6) $R^1$=perfluorobutyl
(I-7) $R^1$=perfluoropentyl
(I-8) $R^1$=perfluorohexyl
(I-9) $R^1$=perfluoro(1-methyl-2-oxabutyl)
(I-10) $R^1$=perfluoro(1,4-dimethyl-2,5-dioxaoctyl)
(I-11) $R^1$=perfluorocyclohexyl
(I-12) $R^1$=perfluoroheptyl
(I-13) $R^1$=perfluorooctyl
(I-14) $R^1$=perfluorodecyl
(I-15) $R^1$=perfluoroundecyl
(I-16) $R^1$=perfluorododecyl
(I-17) $R^1$=perfluoro(1-methyl-2-oxahexyl)
(I-18) $R^1$=perfluorocyclopentyl
(II-1) $R^2$=CH$_3$
(II-2) $R^2$=K
(II-3) $R^2$=C$_2$H$_5$
(II-4) $R^2$=cyclohexyl
(II-5) $R^2$=Na

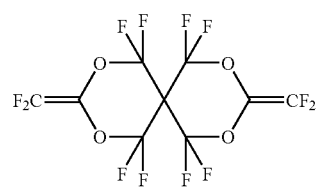

(V)

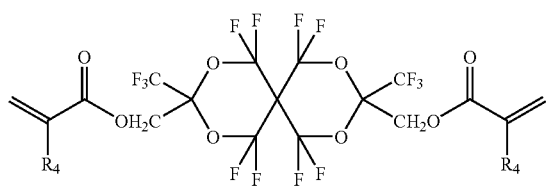

(VI)

(VI-1) $R^4$=H
(VI-2) $R^4$=F
(VI-3) $R^4$=CH$_3$
(VI-4) $R^4$=CF$_3$

The method of producing the fluorine-containing spiroacetal compound represented by formula (A) of the present invention will be explained below.

The fluorine-containing spiroacetal compound represented by the above formula (A) can be produced by steps including the step of fluorinating a spiroacetal compound obtained by reacting an acyloxyacetone or pyruvate with a pentaerythritol.

The fluorine-containing spiroacetal compound represented by formulae (A) may be produced, for example, using a hydroxyacetone 1 or a pyruvate 4 as a starting material, as shown in the following scheme (I).

In the following scheme (1), the production method of the present invention includes at least the step of fluorinating a spiroacetal 3 or 5 obtained by reacting an acyloxyacetone 2 or a pyruvate 4 with pentaerythritol, to obtain a fluorine-containing compound (I) or 6. Of these steps, the production method of the present invention preferably includes steps including the step of fluorinating the spiroacetal compound obtained by reacting an acyloxyacetone with a pentaerythritol.

Substituents in the compounds described in the following scheme will be explained below.

In the following reaction scheme, $R^{11}$ represents an alkyl or cycloalkyl group, which may have a fluorine atom or a substituent explained with regard to $R^2$. $R^{12}$ represents an alkyl or cycloalkyl group, which may have a fluorine atom or a substituent explained with regard to $R^2$. $R^{12}$ is preferably an alkyl group. Rf$^{12}$ represents an alkyl or cycloalkyl group obtained by substituting at least one of hydrogen atoms in $R^{12}$ with a fluorine atom(s). $X^1$ is a halogen atom.

$R^1$ and $R^2$ have the same meanings as defined in formula (A), $R^4$ has the same meaning as defined in formula (VI), and preferred ranges thereof are also as described with regard to these groups.

The above groups will be further explained below.

The alkyl group for $R^{11}$ is preferably a linear or branched alkyl group having 1 to 20 carbon atoms, preferably 2 to 10 carbon atoms; and the cycloalkyl group for $R^{11}$ is preferably a cycloalkyl group having 3 to 20 carbon atoms, preferably 5 to 10 carbon atoms. These groups (substituents) may have the above-described substituents. The alkyl group for $R^{11}$ may have an ether bond in its alkyl chain, and such an alkyl group is also preferred. As the substituent that the above alkyl group may have, preferred are halogen atoms, such as fluorine, chlorine, bromine, and iodine atoms. In the cycloalkyl group represented by $R^{11}$, the substituent on the cycloalkyl group is preferably a substituted alkyl group substituted by a halogen atom, or an alkyl group that may have an ether bond in its alkyl chain. $R^{11}$ is preferably an alkyl group rather than a cycloalkyl group.

$R^{11}$ may be an alkyl group or cycloalkyl group containing no fluorine atom; such as methyl, ethyl, propyl, cyclopentyl, or cyclohexyl. However, $R^{11}$ is preferably an alkyl group or cycloalkyl group containing a fluorine atom; and more preferably a fluorine-atom-containing alkyl group or fluorine-atom-containing cycloalkyl group, which would make the content of fluorine atom in the compound 3 be 30 mass % or more. Examples of such an alkyl group or cycloalkyl group include perfluoroethyl, perfluoropropyl, perfluoroisopropyl, perfluorobutyl, perfluoropentyl, perfluorohexyl, perfluoro(1-methyl-2-oxapentyl), perfluoro(1,4-dimethyl-2,5-dioxaoctyl), perfluorocyclohexyl, perfluoroheptyl, perfluorooctyl, perfluorodecyl, perfluoroundecyl, perfluorododecyl, 2H-tetrahydroethyl, 4H-octafluorobutyl, 6H-dodecafluorohexyl, and 8H-hexadecafluorooctyl.

$X^1$ represents a halogen atom, such as a fluorine atom, a chlorine atom, a bromine atom, and an iodine atom, and preferably a fluorine atom or a chlorine atom.

$R^{12}$ is preferably an alkyl or cycloalkyl group as specified with regard to $R^{11}$, and preferred alkyl and cycloalkyl groups are also as described with regard to $R^{11}$.

$R^{12}$ is preferably an alkyl group, more preferably an alkyl group having a fluorine atom, particularly preferably an alkyl group that contains fluorine atoms such that the fluorine content in the compound 5 would be 30 mass % or more. Examples of such an alkyl group include 1H,1H-pentafluoropropyl, 1H,1H-heptafluorobutyl, 1H,1H,2H,2H-nonafluorohexyl, 1H,1H,2H,2H,3H,3H-nonafluoroheptyl, 1H,1H,2H,2H-tridecafluorooctyl, 1H, 1H,2H,2H,3H,3H-tridecafluorononyl, 1H,1H,2H,2H-heptadecafluorodecyl, 2,5-dimethyl-3,6-dioxa-1H,1H-heptadecafluorononyl, 5-methyl-1H,1H,2H,2H-undecafluorohexyl, 7-methyl-1H,1H,2H,2H-pentadecafluorooctyl, 1H,1H,3H-tetrafluoropropyl, 1H,1H,5H-octafluoropentyl, 1H,1H,7H-dodecafluoroheptyl, 1H,1H,9H-hexadecafluorononyl, 2H-hexafluoro-2-propyl, and 1H,1H,3H-hexafluorobutyl.

$Rf^{12}$ is preferably a perfluoroalkyl group obtained by substituting fluorine atoms for all hydrogen atoms in $R^{12}$.

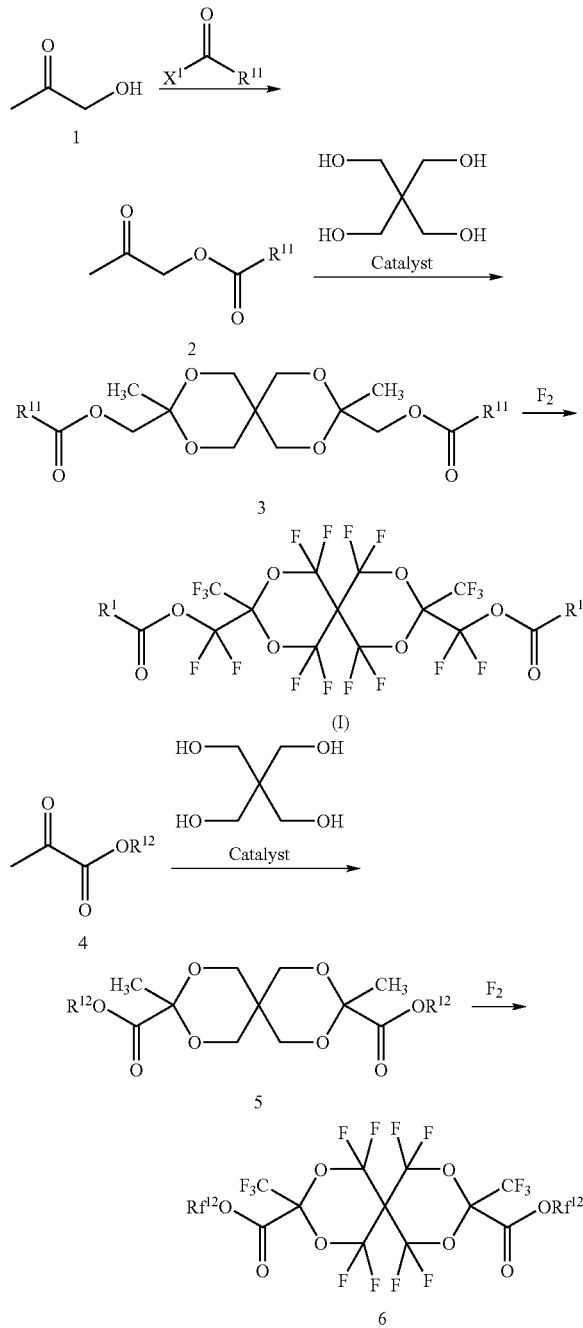

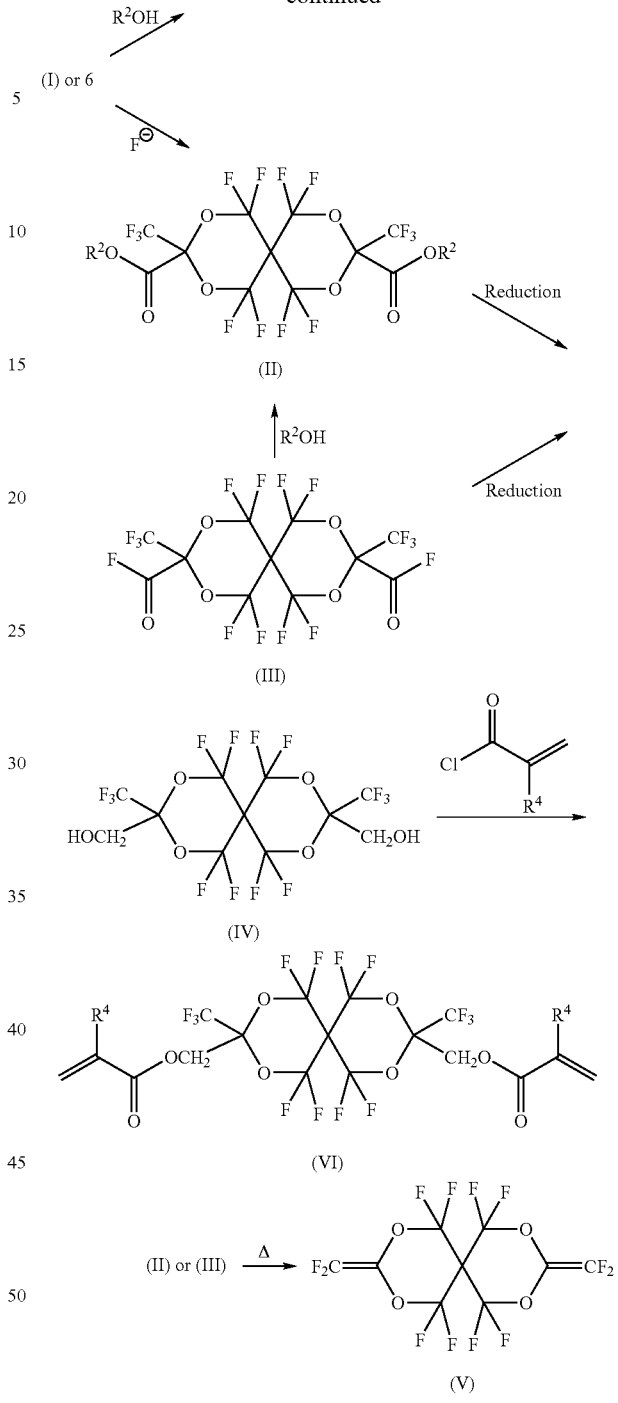

The production process will be further explained below with reference to the above scheme (I).

The acyloxyacetone is preferably represented by the above compound 2, and it can be obtained, for example, by a reaction between a hydroxyacetone 1 and a carboxylic acid halide. On the other hand, the pyruvate is preferably represented by the above compound 4, and it is commercially available or can be easily synthesized by esterification of a pyruvic acid.

In the present invention, the fluorine-containing spiroacetal compound represented by the above formula (A) can be produced by steps including the steps of reacting an acyloxyacetone (compound 2) or pyruvate (compound 4) with pentaerythritol, in more specific, subjecting these compounds to dehydrative condensation, to synthesize a spiroacetal compound (compound 3 or 5), and then fluorinating the thus-obtained spiroacetal compound (compound 3 or 5).

Herein, the compound represented by formula (I) can be synthesized by obtaining the compound 3 from the compound 2 in the above reaction scheme (the compound 2 is synthesized from a compound 1, in the above reaction scheme) and fluorinating the compound 3.

The compound represented by formula (U) can be synthesized by reacting the thus-obtained compound represented by formula (I) with $R^2OH$ or by reacting a compound 6 (the compound 6 can be obtained by obtaining a compound 5 from a compound 4 and fluorinating the compound 5) with $R^2OH$. Further, the compound represented by formula (II) can be also obtained by reacting the compound represented by formula (I) or the compound 6 with $F^-$ ion and reacting the thus-obtained compound represented by formula (III) with $R^2OH$. In the case of obtaining a compound represented by formula (II) in which $R^2$ is a hydrogen atom, an alkali metal, or an alkaline earth metal, such compound represented by formula (II) can be as well synthesized by hydrolysis of a compound represented by formula (II) in which $R^2$ is an alkyl or cycloalkyl group or by hydrolysis of a compound represented by formula (III).

The compound represented by formula (III) can be synthesized by reacting the compound represented by formula (Q or the compound 6 with $F^-$ ion, as described above. It is also a preferable embodiment of the present invention that the compound represented by formula (III) is synthesized by thermal decomposition of the compound represented by formula (I) or the compound 6, although this is not shown in the above reaction scheme.

The compound represented by formula (IV) can be synthesized by reducing the thus-obtained compound represented by formula (II) or formula (III).

The compound represented by formula (V) can be synthesized by thermal decomposition of the thus-obtained compound represented by formula (II) or formula (III).

The compound represented by formula (A) wherein X is $>C(CF_3)(Y)$, Y is $—CH_2OR^3$, and $R^3$ is an acyl group can be synthesized by acylation of the compound represented by formula (IV). The acylating agent can be selected from an acyl halide having a corresponding acyl portion or an organic acid anhydride, and an organic acid is also preferably used. In the above reaction scheme, of these compounds, the compound represented by formula (VI) is described as a typical compound. That is, the acylating agent for the compound represented by formula (VI) is particularly preferably an acrylic acid derivative represented by $Cl—COC(R^4)=CH_2$, as will be explained later.

Each step in the above scheme (I) will be explained in detail.

The conversion into an acyloxyaceton (the compound 2) by a reaction between the hydroxyacetone 1 and the carboxylic acid halide may be carried out in usual conditions as described, for example, in "Dai-4-Han, Jikken Kagaku Koza 22, Yuki-Gosei IV, —San/Amino san/Peptide—(4th edition, Courses in Experimental Chemistry 22, Organic Synthesis IV, —Acids/Amino acids/Peptides—)", The Chemical Society of Japan, Maruzen, pp. 50-51.

The synthesis to obtain a spiroacetal 3 or 5 from the compound 2 or 4 and pentaerythritol may be carried out according to methods described in, for example, J. Org. Chem., 26, 2515 (1961); Tetrahedoron, 60, 4789 (2004); and Chem. Ber., 61, 790 (1928).

Specifically, the compound 2 or 4 and pentaerythritol undergo a dehydration condensation reaction. As to this dehydration reaction, any method may be used insofar as it can remove or separate the water to be generated under the reaction condition. It is however preferable to use a method in which water is removed in the presence of an acid catalyst by azeotropic distillation or a method in which the reaction is run in the presence of a dehydrating agent.

At this time, the amount of pentaerythritol to be used is preferably 0.1 to 5 equivalents, more preferably 0.2 to 1 equivalent, and particularly preferably 0.3 to 0.6 equivalents to the amount of the compound 2 or 4.

Examples of the acid catalyst include hydrogen chloride, hydrogen bromide, sulfuric acid, phosphoric acid, ammonium chloride, sulfonic acid compounds (for example, methanesulfonic acid, benzenesulfonic acid, p-toluenesulfonic acid (monohydrate)), carboxylic acid compounds (for example, acetic acid, propionic acid, butanoic acid, adipic acid, and benzoic acid), various Lewis acids (for example, boron trifluoride etherate, aluminum chloride, and zirconium oxide), and various solid acid catalysts (for example, Nafion® (trade name), Amberlite® (trade name, acidic type), and Montmorillonite K10 (trade name)). These compounds may be used in combinations. Among these compounds, p-toluenesulfonic acid monohydrate is preferable. The amount of the above acid catalyst to be used is preferably 0.001 to 2 equivalents, and more preferably 0.01 to 0.5 equivalents, to the amount of the compound 2 or 4.

When removing water by azeotropic distillation, a Dean-Stark trap is preferably used. Also, when removing water by a dehydrating agent, examples of the dehydrating agent include magnesium sulfate, sodium sulfate, zeolite, and molecular sieves. The dehydrating agent is preferably used in an amount larger than the amount sufficient to retain the water generated in the reaction. The dehydrating agent may be used in the reaction system, or out of the reaction system, for example, by keeping the dehydrating agent in the reflux tube.

The reaction may be conducted in no solvent or in a solvent. Examples of the solvent that can be used include benzene, toluene, xylene, petroleum ether, N,N-dimethylformamide, N,N-diethylacetamide, 1-methyl-2-pyrrolidone, 1,3-dimethyl-2-imidazolidinone, dimethylsulfoxide (DMSO), sulfolane, carbon tetrachloride, chloroform, hexane, heptane, and cyclohexane, and mixtures of these solvents. Among these solvents, toluene is more preferable. The amount by mass of the solvent is preferably 1 to 100 times and more preferably 2 to 50 times that of the compound 2 or 4. The reaction temperature is preferably 0 to 200° C. and more preferably 50 to 120° C. The reaction time depends on the type and amount of acid to be used, the type of solvent, and the reaction temperature. The reaction is generally conducted within 12 hours and preferably 6 hours, by controlling these factors.

As the fluorinating reaction converting the compound 3 into the compound represented by formula (I) or the compound 5 into the compound 6, it is known to use a method using cobalt trifluoride, an electrolytic fluorinating method, a method using fluorine gas to carry out fluorination directly in a liquid phase (hereinafter referred to as "liquid-phase direct fluorinating method"), or the like. These methods may be utilized in the present invention. In the fluorinating reaction according to the method using cobalt trifluoride or the electrolytic fluorinating method, there are problems concerning a rise in isomerization reaction and cutting or recombination reaction of a main chain, and it is therefore difficult to obtain a desired compound with a high purity. It is therefore more preferable to use the liquid phase-direct fluorinating method in the present invention.

The fluorinating reaction according to the liquid-phase direct fluorinating method may be carried out in the same methods that are described in, for example, U.S. Pat. No. 5,093,432 and WO00/56694.

The conversion from the compound represented by formula (I) or the compound 6 into the compound represented by formula (II), especially the compound represented by formula (II) with $R^2$ being an alkyl group or a cycloalkyl group, may be carried out by reacting an alcohol represented by $R^2OH(R^2$ represents an alkyl group or a cycloalkyl group) with the compound represented by formula (I) or the compound 6. The reaction temperature is preferably −20 to 100° C. and more preferably 0 to 50° C. In this reaction, a solvent may be used or the reaction may be conducted in no solvent. Also, the reaction may be conducted in the presence of a base or in the presence of no base.

Examples of the solvent that can be used may include dichloromethan, chloroform, carbon tetrachloride, diethyl ether, tetrahydrofuran, acetone, ethyl acetate, hexane, toluene, xylene, acetonitrile, the solvents used in the above liquid-phase fluorinating reaction {for example, perfluoroalkane compounds (trade name: FC-72, manufactured by Sumitomo 3M Ltd.), perfluoroether compounds (trade name: FC-75, FC-77, manufactured by Sumitomo 3M Ltd.), perfluoropolyether compounds (trademark: Krytox, manufactured by DuPont; trademark: Fomblin, manufactured by AUSIMONT; trademark: Galden, manufactured by AUSIMONT; trade name: Demnam, manufactured by Daikin Industries, Ltd.), chlorofluorocarbon compounds (for example, CFC-11 and CFC-113), chlorofluoropolyether compounds, perfluorotrialkylamine compounds, and inert fluids (trademark: Fluorinert, manufactured by Sumitomo 3M Ltd.)}, and mixtures of these solvents. The amount by mass of the solvent is preferably 1 to 100 times and more preferably 2 to 50 times that of the compound represented by formula (I) or the compound 6.

Examples of the base which may be used include organic bases, such as pyridine, triethylamine, and N,N-diisopropylethylamine; and inorganic bases, such as sodium hydroxide, potassium hydroxide, potassium carbonate, sodium carbonate, sodium bicarbonate, and potassium bicarbonate. Also, an alkali metal fluoride, such as sodium fluoride, potassium fluoride, or cesium fluoride may be used as hydrogen fluoride trapping agent.

The amount of the base to be used in the present invention is preferably 0.5 to 10 equivalents and more preferably 1 to 3 equivalents to the amount of the compound represented by formula (I) or the compound 6.

Though there is no particular limitation to the amount of $R^2OH$, the amount of $R^3OH$ is preferably 4 equivalents or more and more preferably 4 to 20 equivalents to the amount of the compound represented by formula (I) or the compound 6, to complete the reaction.

The compound represented by formula (II) with $R^2$ being a hydrogen atom, an alkali metal, or an alkaline earth metal can be easily obtained by the (alkali-) hydrolysis of any one of the compound represented by formula (I), the compound 6, and the compound represented by formula (II) with $R^2$ being an alkyl group or cycloalkyl group.

The compound represented by formula (I) or the compound 6 may be converted into the compound represented by formula (III) by thermal decomposition. This thermal decomposition is preferably carried out in the presence of an alkali metal fluoride, such as sodium fluoride, potassium fluoride, or cesium fluoride. The amount of the alkali metal fluoride to be used is preferably 0.01 to 5 equivalents and more preferably 0.1 to 1 equivalent to the amount of the compound represented by formula (I) or the compound 6. The reaction temperature is preferably 50 to 300° C. and more preferably 100 to 250° C. The reaction may be conducted in either a vapor phase or a liquid phase. In the case of the liquid phase reaction, any solvent may be used without any particular limitation insofar as it is compatible with the compound represented by formula (I) or the compound 6 and is inert to the compound represented by formula (I) or the compound 6 and to the product. For example, perfluoropolyether compounds or chlorofluoropolyether compounds as mentioned above may be used. It is however preferable to conduct the reaction in the presence of no solvent in consideration of separating the solvent from the product.

The compound represented by formula (III) may be converted into the compound represented by formula (II) in the same conversion condition under which the compound represented by formula (I) is converted into the compound represented by formula (II).

The compounds represented by formula (II) or (III) may be converted into the compound represented by formula (IV) by a reduction reaction. As the reduction reaction, use can be made of any of various reduction methods which are described in, for example, "Dai-4-Han, Jikken Kagaku Koza 26, Yuki-Gosei VIII, —Husei-Gosei/Kangen/To/Hyosiki-Kagobutu—(4th edition, Courses in Experimental Chemistry 26, Organic Synthesis VIII, —Asymmetric synthesis/Reduction/Saccharide/Labeled compound—)", The Chemical Society of Japan, Maruzen, pp. 159-266. Preferable examples of the reduction method include a method using a metal hydrogen complex compound, such as sodium borohydride, lithium aluminum hydride, and bis(2-methoxyethoxy)aluminum sodium hydride (trade name: Red-A1, Vitride) (see, for example, references such as J. Am, Chem. Soc, 116, 4135 (1994), J. Org. Chem., 26, 2943 (1961), J. Org. Chem., 41, 1470 (1976), and J. Am. Chem. Soc, 115, 8954 (1993)), and a method by catalytic reduction using a hydrogen/transition metal catalyst (see for example, U.S. Pat. No. 2,666,797).

The compound represented by formula (V) can be obtained by thermal decomposition of the compound represented by formula (II) (in which $R^2$ is preferably an alkali metal or an alkaline earth metal, more preferably sodium or potassium) or the compound represented by formula (III). For conditions for the thermal decomposition, reference can be made, for example, to Methods of Organic Chemistry, 4, Vol. 10b, Part 1, p. 703, J. Fluorine Chem., 94, 65 (1999), J. Fluorine Chem., 123, 43 (2003), J. Org. Chem., 34, 1841 (1969), J. Org. Chem., 51, 326 (1986), and the like.

The compound represented by formula (IV) can be converted to the compound represented by formula (VI) by esterification thereof with an acrylic acid derivative. The acrylic acid derivative can be selected from a carboxylic acid represented by $CH_2=CH(R^4)CO_2H$, an acid halide represented by $CH_2=CH(R^4)COX^1$ (in which $X^1$ is a halogen atom, such as a fluorine atom, a chlorine atom, a bromine atom, or iodine atom, preferably a chlorine atom; and $R^4$ is as defined in formula (VI)), or an acid anhydride represented by $[(CH_2=CH(R^4)CO)_2]O$ ($R^4$ is as defined in formula (VI)). The esterification with the compound represented by formula (IV) can be carried out under such general conditions as described, for example, in "Dai-4-Han, Jikken Kagaku Koza 22, Yuki-Gosei IV, San/Amino-san/Peptide (4th Edition, Courses in Experimental Chemistry 22, Organic Synthesis IV, —Acids/Amino acids/Peptides)", pp. 43-53, edited by The Chemical Society of Japan, Maruzen Co., Ltd.

A polyester may be produced by condensation-polymerizing the difunctional ester represented by formula (II) or an acid fluoride represented by formula (III) with a polyfunctional alcohol or phenol (for example, a difunctional alcohol represented by formula (IV) according to the present invention, ethylene glycol, 1,3-propanediol, bisphenol, and hydroquinone). The method of producing the polyester may be carried out according to methods described, for example, in "Dai-4-Han, Jikken Kagaku Koza 28, Kobunshi Gosei (4th Edition, Courses in Experimental Chemistry 28, Polymer Synthesis)", The Chemical Society of Japan, Maruzen, pp. 217-231.

Also, the difunctional ester represented by formula (II) according to the present invention or an acid fluoride represented by formula (III) may be condensation-polymerized with a polyfunctional amine or aniline (for example, ethylenediamine, 1,3-diaminopropane, bis(4-aminophenyl)ether, and 4,4'-diaminodiphenylmethane), to produce a polyamide. The method of producing a polyamide may be carried out according to the method described, for example, in "Dai-4-Han; Jikken Kagaku Koza 28, Kobunshi Gosei (4th Edition, Courses in Experimental Chemistry 28, Polymer Synthesis)", The Chemical Society of Japan, Maruzen, pp. 260-277.

Further, the difunctional alcohol represented by formula (IV) according to the present invention may be condensation-polymerized with a polyfunctional electrophilic agent (for example, 1,2-dibromoethane, 1,3-dibromopropane, 4,4'-dichlorobenzophenone, 4,4'-difluorobenzophenone, and bis(4-chlorophenyl)sulfone), to produce a polyether. The method of producing the polyether may be carried out according to conditions of aromatic nucleophilic substitution polymerization as described, for example, in "Dai-4-Han, Jikken Kagaku Koza 28, Kobunshi Gosei (4th Edition, Courses in Experimental Chemistry 28, Polymer Synthesis)", The Chemical Society of Japan, Maruzen, p. 185.

The polyester, polyamide, polyether and the like obtained in this manner have a high fluorine content and have characteristics, such as high light transmittance, low-refractive index, and water/oil repellency, which are specific to a fluorine-containing polymer.

The present invention will be described in more detail based on the following examples, but the invention is not intended to be limited thereto.

EXAMPLES

Example 1

Specific examples of preparations of the compound represented by formula (A) will be explained below.

The compounds represented by formulae (I-1), (II-1), (III), (IV), or (V), and compounds represented by formula (II-2) or (VI-1) were produced according to the following scheme.

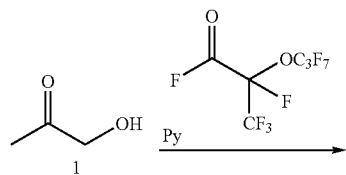

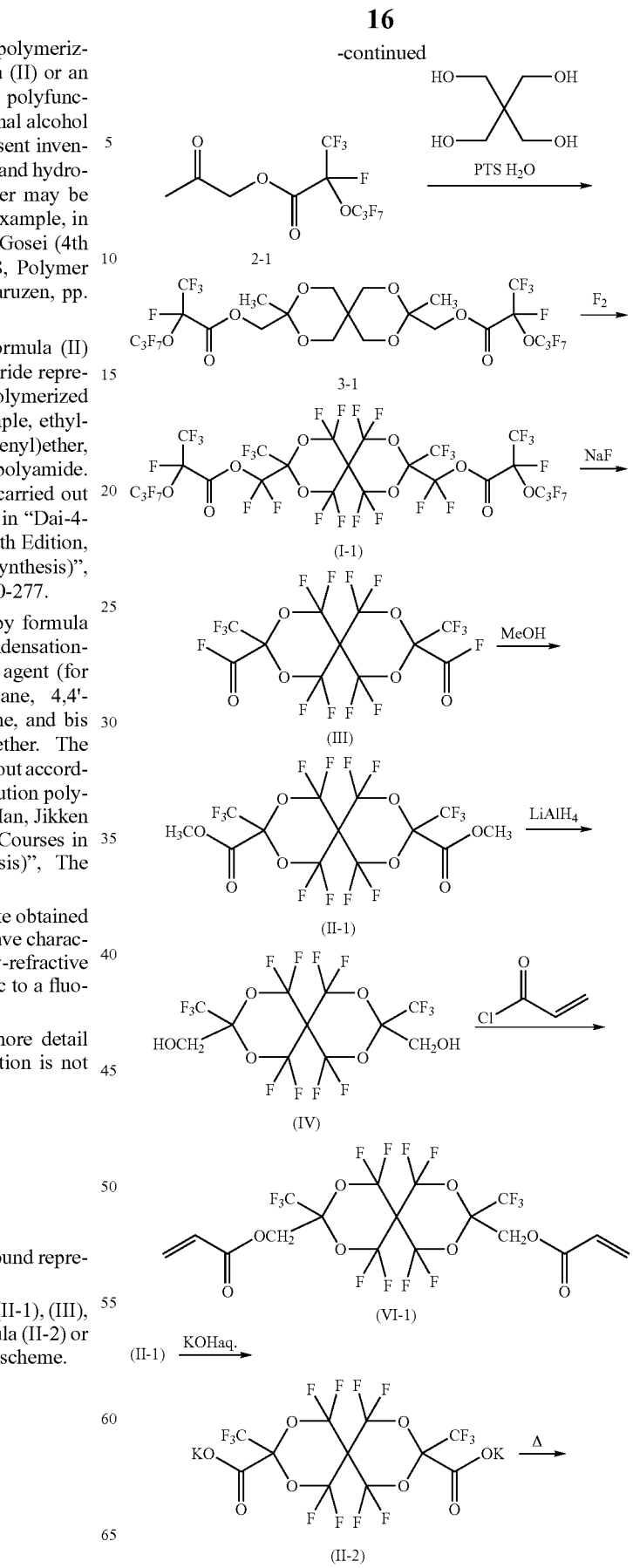

-continued

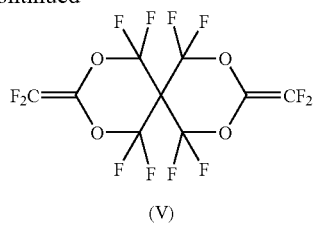

(V)

Production of Compound 2-1

Undecafluoro(2-methyl-3-oxahexanic acid)fluoride (10 g) was added dropwise to an ethyl acetate solution (100 ml) containing hydroxyacetone (7.4 g) and pyridine (8.1 ml) at room temperature (25° C.). After the mixture was stirred at room temperature for 2 hours, the reaction solution was poured into an aqueous dilute hydrochloric acid solution. After the reaction solution was fractionated, the organic phase was washed with water and then with saturated brine and dried over magnesium sulfate. The concentrated residue was purified by column chromatography (developing solvent: ethyl acetate/hexane), to obtain Compound 2-1 (10.2 g, yield: 88%).

$^1$H NMR (CDCl$_3$) δ 2.22 (s, 3H), 4.85 (d, J=16.2 Hz, 1H), 4.96 (d, J=16.2 Hz, 1H)

$^{19}$F NMR (CDCl$_3$) δ −80.3 (1F), −81.8 (3F), −82.5 (3F), −86.7 (1F), −130.2 (2F), −132.8 (1F)

Production of Compound 3-1

Compound 2-1 (9.9 g), pentaerythritol (1.74 g), p-toluenesulfonic acid monohydrate (0.25 g), and toluene (50 ml) were refluxed while dehydrating, for 4 hours. The reaction solution was washed with an aqueous sodium bicarbonate solution, water, and saturated brine, and then dried over sodium sulfate. The concentrated residue was purified by column chromatography (developing solvent: ethyl acetate/hexane), to obtain Compound 3-1 (5.9 g, yield: 53%).

$^1$H NMR (CDCl$_3$) δ 1.41 (s, 3H), 3.64 to 3.85 (m, 4H), 4.31 (d, J=11.1 Hz, 1H), 4.48 (d, J=11.1 Hz, 1H)

$^{19}$F NMR (CDCl$_3$) δ −80.2 (1F), −81.7 (3F), −82.5 (3F), −86.8 (1F), −130.1 (2F), 132.3 (1F)

Production of Compound Represented by Formula (I-1)

A 300 ml Teflon (trademark) container equipped with a raw-material supply port, a fluorine supply port, a helium-gas supply port, and a discharge port connected with a fluorine trap through a refluxing unit cooled by dry ice, was charged with 180 ml of FC-72, and helium gas was blown therein at a flow rate of 50 ml/min at an internal temperature of 20° C. for 30 minutes. Subsequently, 20% F$_2$/N$_2$ gas was blown at a flow rate of 100 ml/min for 30 minutes. A FC-72 (13.5 ml) solution of Compound 3-1 (4.25 g) and a FC-72 (5 ml) solution of hexafluorobenzene (1 g) were added to the mixture at a flow rate of 6.2 ml/h each while the flow rate of fluorine was kept as it was. Further, 20% F$_2$/N$_2$ gas was blown at a flow rate of 100 ml/min for 30 minutes, and helium gas was blown at a flow rate of 200 ml/min for 30 minutes. FC-72 was concentrated under normal pressure, and then further concentrated under reduced pressure, to obtain Compound represented by formula (I-1) (5.1 g, crude yield: 88%) as almost a single product (oily substance).

$^{19}$F NMR (CDCl$_3$) δ −60.6 to 64.4 (m, 8F), −76.7 (s, 6F), −79.8 to −80.0 (m, 1F), −80.3 to −80.6 (m, 1F), 82.0 (m, 6F), 82.1 (s, 6F), −83.4 to −83.8 (m, 4F), −86.7 (bs, 1F), −86.9 (bs, 1F), −130.2 (s, 4F), −132.0 (s, 1F), −132.1 (s, 1F)

Production of Compounds Represented by Formulae (III) and (II-1)

Compound represented by formula (I-1) (5.1 g) obtained above and sodium fluoride (0.06 g) were stirred at 100 to 120° C. for 24 hours. At this time, the reactor was equipped with a water-cooling type condenser, to reflux low-boiling products. Compound represented by formula (III) (0.5 g, yield: 22%) was obtained by distillation earned out under reduced pressure.

Also, methanol (20 ml) was added to the distillation residue and the mixture was stirred at room temperature for 3 hours. The reaction solution was poured into an ethyl acetate/sodium bicarbonate solution. The organic phase was washed with water and then with saturated brine and dried over magnesium sulfate. The concentrated residue was purified by column chromatography (developing solvent: ethyl acetate/hexane), to obtain Compound represented by formula (II-1) (1.2 g, yield: 51%).

Formula (III): $^{19}$F NMR (CDCl$_3$) δ 30.2 to 30.3 (m, 2F), −62.8 to −64.2 (m, 4F), −70.6 to −71.8 (m, 4F), −80.9 to −81.0 (m, 6F); Melting point: 26 to 28° C.; Boiling point: 135° C.

Formula (II-1): $^1$H NMR (CDCl$_3$) δ 3.99 (s, 3H)

$^{19}$F NMR (CDCl$_3$) δ −62.5 to −63.8 (m, 4F), −69.9 to −71.3 (m, 4F), −81.2 (s, 3F), −81.4 (s, 3F); Melting point: 48 to 55° C.

Production of Compound Represented by Formulae (IV)

Lithium aluminum hydride (0.038 g) was added to a diethyl ether (10 ml) solution of the compound represented by formula (II-1) (0.28 g) at 5° C. The mixture was stirred at room temperature for 4 hours. Then, an aqueous dilute hydrochloric acid was gradually added to the reaction solution. The resulting solution was extracted with ethyl acetate, and the organic phase was washed with water and then saturated brine, and then dried over magnesium sulfate. The concentrated residue was purified by column chromatography (developing solvent: ethyl acetate/hexane), to obtain Compound represented by formula (IV) (0.2 g, yield: 80%).

$^1$H NMR (CDCl$_3$) δ 2.20 (bs, 1H), 4.21 (bs, 2H), $^{19}$F NMR (CDCl$_3$) δ −56.2 to |58.6 (m, 4F), 66.0 to |67.3 (m, 4F), 80.9 to 81.0 (m, 6F),

Melting point: 106 to 108° C.

Production of Compound (VI-1)

Potassium carbonate (4.8 g) was added to a solution of the compound represented by formula (IV) (3.7 g) dissolved in 1-methyl-2-pyrrolidone (30 ml), and further, acrylic acid chloride (2.4 ml) was gradually added dropwise. The reaction solution was stirred at room temperature for 3 hours, and then the reaction solution was poured into ethyl acetate (150 ml)/diluted hydrochloride acid (150 ml). The organic layer was washed with a sodium hydrogencarbonate aqueous solution, water, and saturated brine, and dried over magnesium sulfate. The concentrated residue was purified by column chromatography (developing solvent: ethyl acetate/hexane=1/5), to give Compound (VI-1) (3.5 g, yield: 78%).

$^1$H NMR (CDCl$_3$) δ 4.75 (s, 4H), 5.98 (dd, J=10.5 Hz, 1.2 Hz, 2H), 6.16 (dd, J=17.1 Hz, 10.5 Hz, 2H), 6.51 (dd, J=17.1 Hz, 1.2 Hz, 2H)

$^{19}$F NMR (CDCl$_3$) δ −57.0 to −58.3 (m, 4F), −66.1 to −67.0 (m, 4F), −81.2 (s, 3F), −81.3 (s, 3F)

Melting point: 34 to 35° C.

Production of Compound Represented by Formula (V)

To a solution of Compound represented by formula (II-1) (16.2 g) dissolved in methanol (200 ml)/water (40 ml) was dropwise added 10 ml of an 8N potassium hydroxide aqueous solution, at room temperature. The reaction solution was stirred at room temperature for 2 hours, and the solvent was distilled off under reduced pressure. To the concentrated residue was added 30 ml of water, and further, a concentrated hydrochloric acid aqueous solution was added dropwise until a pH testing paper showed acidity. Precipitated white crystals were recovered by filtration, and then dispersed in water (30 ml), and a 1N potassium hydroxide aqueous solution was added dropwise, to adjust to a pH of 8. The reaction solution was concentrated under reduced pressure, and the residue was fully dried at 100° C. with a vacuum pump, to give Compound (II-2) (16.5 g, yield: 93%). The thus-obtained Compound (II-2) was thermally decomposed at 280° C. under reduced pressure (4 mmHg), and a volatile component was collected with a trap at −78° C. The thus-obtained liquid was distilled under reduced pressure, to give Compound represented by formula (V) (0.98 g, yield: 74%).

$^{19}$F NMR (CDCl$_3$) δ −70.7 (s, 8F), 111.2 (s, 4F); b.p. 55° C. (20 mmHg)

Reference Example 1

Compound (VI-1) (2 g) and Irgacure 907 (trade name, a photopolymerization initiator manufactured by Ciba-Geigy AG) (0.1 g) were dissolved in methyl ethyl ketone, to prepare a 30 mass % solution, and the solution was filtered with a polytetrafluoroethylene filter having a pore size of 0.25 μm. The thus-prepared curable resin composition was applied onto a PET substrate with a bar coater. The solvent was dried off (at room temperature for 30 minutes and at 120° C. for 2 minutes), and then a formed coating was irradiated with ultraviolet light (500 mJ, twice) in nitrogen atmosphere, and farther heated at 120° C. for 2 minutes, to give a transparent cured resin coating film.

Further, cured resin coating films were formed in the same manner as above, except that Compound (VI-1) was replaced with an equimolar amount of Compound (VII) or Compound (VIII).

The thus-prepared cured resin coating films of Compound (VI-1), (VII), and (VIII) were consisted of amorphous polymers.

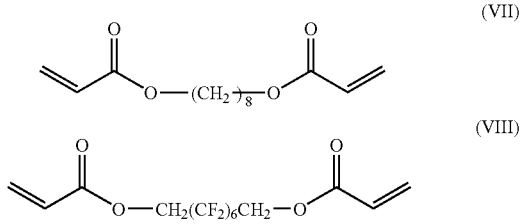

These films were evaluated for pencil hardness, refractive index, adherence, and contact angle, and the following Table 1 shows the results.

The evaluations were made according to the following methods.
Pencil hardness: Measured according to JIS K5400.
Refractive index: Measured with an Abbe refractometer (manufactured by ATAGO CO., LTD).
Adherence: A peel test was carried out according to JIS K5400. (○: No peeling, Δ: Peeled by less than 5%, X: Peeled by 5% or more)
Contact angle: Measured for a contact angle to pure water with a contact angle meter (manufactured by Kyowa Interface Science Co., Ltd.).
Chemical resistance: A 5% sodium hydroxide aqueous solution in an amount of 0.5 ml was dropped on a film surface. After the film was left for 12 hours, the film surface was wiped. The appearance of the film surface thereafter was observed. (○: No change, Δ: A slight change was observed, x: A great change was observed).

TABLE 1

Evaluation of performances of difunctional acrylate cured coating films

| Compound No. | Pencil hardness | Refractive index | Adherence | Contact angle | Chemical resistance |
|---|---|---|---|---|---|
| (VI-1) | H | 1.419 | ○ | 110° | ○ |
| (VII) | H | 1.495 | ○ | 65° | Δ |
| (VIII) | H | 1.421 | Δ | 110° | ○ |

From the above Table 1, the polymer using Compound (VII), which was a comparative example, exhibited a large refractive index, poor water repellency (which was represented by an extremely small contact angle), and insufficient chemical resistance. The polymer using Compound (VIII), which was also a comparative example, exhibited insufficient adherence. In contrast, the polymer using Compound (VI-1) according to the present invention was excellent in all of pencil hardness, refractive index, adherence, contact angle, and chemical resistance.

Reference Example 2

A mixture of 0.5 g of Compound represented by formula (V) and 6 ml of perfluorobenzoyl peroxide was fully deoxidized by nitrogen bubbling, and was allowed to stand as it was in a sealed state at 30° C. for 3 days. The resultant solid was recovered by filtration, washed with acetone and then dried, to give a white polymer (0.2 g, m.p. 300° C. or higher). When a pin wear amount was measured with a FALEX wear tester, manufactured by Falex Corporation (conditions: 80° C., 250 lb, 1 hour), using an ester oil containing 1 mass % of the white polymer, a great decrease in wear amount was observed as compared with a case where the above polymer was not added.

INDUSTRIAL APPLICABILITY

The compounds of the present invention are each useful as a raw material monomer of a fluorine-containing polymer that has characteristics, such as chemical resistance, weather fastness, water/oil repellency, less intermolecular interaction tendency, low refractive index, and high light transmittance; or as a precursor of such a monomer.

Further, according to the producing method of the present invention, fluorine-containing compounds each having a spiroacetal structure can be produced with high yield.

Furthermore, according to the producing method of the present invention, the aforementioned fluorine-containing compound having a spiroacetal structure can be easily produced from less expensive materials without employing complicated procedures.

Polymers of the fluorine-containing spiroacetal compound represented by formula (A) are excellent in chemical resistance, weather fastness, and optical properties, and can be utilized in various applications, such as optical waveguides.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. A fluorine-containing spiroacetal compound represented by the following formula (A):

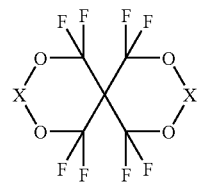

(A)

wherein X represents >C(CF$_3$)(Y) or >C=CF$_2$, in which Y represents —CF$_2$OCOR$^1$, —COOR$^2$, —COF, or —CH$_2$OR$^3$, R$^1$ represents an alkyl or cycloalkyl group having at least one fluorine atom, R$^2$ represents a hydrogen atom, an alkali metal, an alkaline earth metal, an alkyl group, or a cycloalkyl group, and R$^3$ represents a hydrogen atom or an acyl group; wherein the alkyl or cycloalkyl group for R$^1$ may have a substituent other than fluorine atom; the alkyl or cycloalkyl group for R$^2$ may have a substituent; and the acyl group for R$^3$ may have a substituent.

2. The fluorine-containing spiroacetal compound as claimed in claim 1, wherein the compound represented by formula (A) is a compound represented by any one of the following formulae (I), (II), (III), and (IV):

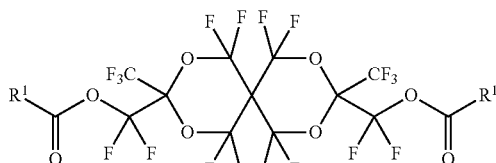

(I)

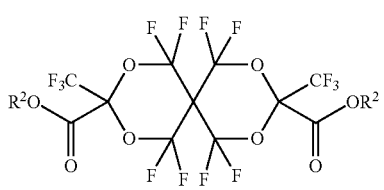

(II)

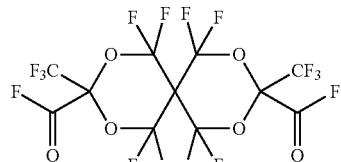

(III)

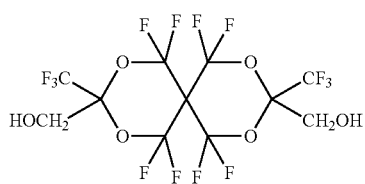

(IV)

wherein R$^1$ represents an alkyl or cycloalkyl group having at least one fluorine atom; R$^2$ represents a hydrogen atom, an alkali metal, an alkaline earth metal, an alkyl group, or a cycloalkyl group; wherein the alkyl or cycloalkyl group for R$^1$ may have a substituent other than fluorine atom, and the alkyl or cycloalkyl group for R$^2$ may have a substituent.

3. The fluorine-containing spiroacetal compound as claimed in claim 1, wherein R$^1$ represents a perfluoroalkyl group.

4. The fluorine-containing spiroacetal compound as claimed in claim 1, wherein, in formula (A), R$^3$ represents a hydrogen atom or —COC(R$^4$)=CH$_2$, in which R$^4$ represents a hydrogen atom, a fluorine atom, a methyl group, or a trifluoromethyl group.

5. A perfluoroester compound represented by formula (I-1)

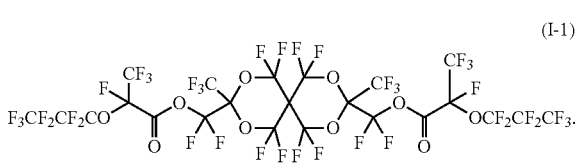

(I-1)

6. A methylester compound represented by formula (II-1)

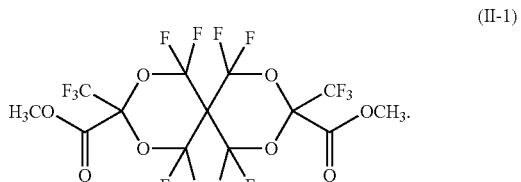

(II-1)

7. A perfluorodiene compound represented by formula (V)

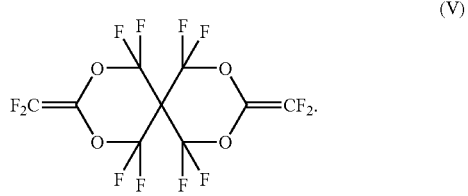

(V)

8. A fluorine-containing diacrylate compound represented by formula (VI):

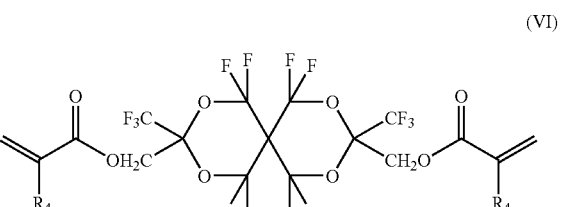

(VI)

wherein R$^4$ represents a hydrogen atom, a fluorine atom, a methyl group, or a trifluoromethyl group.

9. A method of producing a fluorine-containing spiroacetal compound represented by the following formula (A), which comprises the step of fluorinating a spiroacetal compound obtained by reacting an acyloxyacetone or a pyruvate with a pentaerythritol;

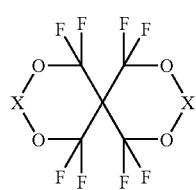

(A)

wherein X represents >C(CF$_3$)(Y) or >C=CF$_2$, in which Y represents —CF$_2$OCOR$^1$, —COOR$^2$, —COF, or —CH$_2$OR$^3$, R$^1$ represents an alkyl or cycloalkyl group having at least one fluorine atom, R$^2$ represents a hydrogen atom, an alkali metal, an alkaline earth metal, an alkyl group, or a cycloalkyl group, and R$^3$ represents a hydrogen atom or an acyl group; wherein the alkyl or cycloalkyl group for R$^1$ may have a substituent other than fluorine atom; the alkyl or cycloalkyl group for R$^2$ may have a substituent; and the acyl group for R$^3$ may have a substituent.

10. A method of producing a fluorine-containing spiroacetal compound represented by the aforementioned formula (A) of claim 9, which comprises the step of fluorinating a spiroacetal compound obtained by reacting an acyloxyacetone with a pentaerythritol.

11. The method as claimed in claim 9, wherein the fluorine-containing spiroacetal compound represented by the aforementioned formula (A) is a compound represented by any one of the following formulae (I), (II), (III), and (IV):

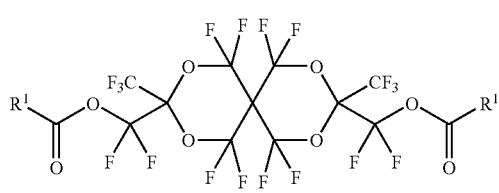

(I)

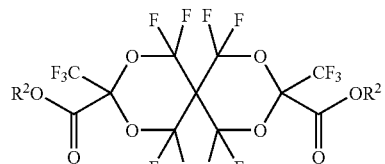

(II)

(III)

(IV)

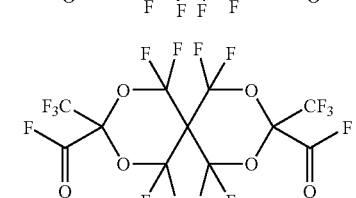

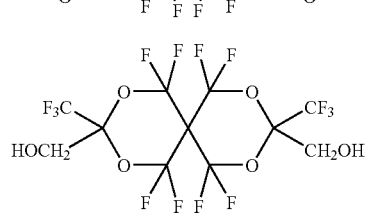

wherein R$^1$ represents an alkyl or cycloalkyl group having at least one fluorine atom; R$^2$ represents a hydrogen atom, an alkali metal, an alkaline earth metal, an alkyl group, or a cycloalkyl group; wherein the alkyl or cycloalkyl group for R$^1$ may have a substituent other than fluorine atom, and the alkyl or cycloalkyl group for R$^2$ may have a substituent.

12. The method as claimed in claim 9, wherein R$^1$ represents a perfluoroalkyl group.

13. The method as claimed in claim 9, wherein, in formula (A), R$^3$ represents a hydrogen atom or —COC(R$^4$)=CH$_2$, in which R$^4$ represents a hydrogen atom, a fluorine atom, a methyl group, or a trifluoromethyl group.

14. The method as claimed in claim 10, wherein the fluorine-containing spiroacetal compound represented by the aforementioned formula (A) is a compound represented by any one of the following formulae (I), (II), (III), and (IV):

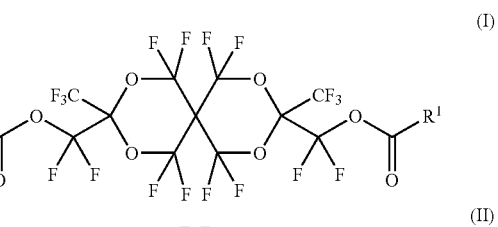

(I)

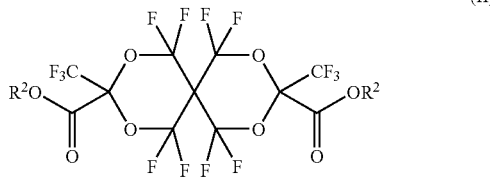

(II)

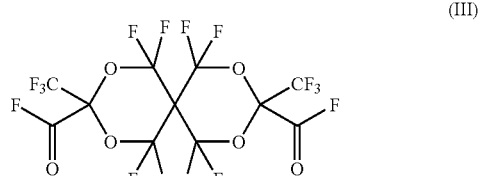

(III)

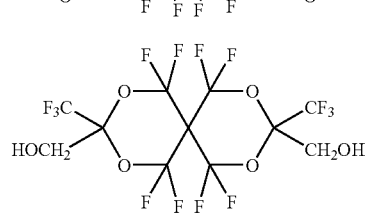

(IV)

wherein R$^1$ represents an alkyl or cycloalkyl group having at least one fluorine atom; R$^2$ represents a hydrogen atom, an alkali metal, an alkaline earth metal, an alkyl group, or a cycloalkyl group; wherein the alkyl or cycloalkyl group for R$^1$ may have a substituent other than fluorine atom, and the alkyl or cycloalkyl group for R$^2$ may have a substituent.

15. The method as claimed in claim 10, wherein R$^1$ represents a perfluoroalkyl group.

16. The method as claimed in claim 10, wherein, in formula (A), R$^3$ represents a hydrogen atom or —COC(R$^4$)=CH$_2$, in which R$^4$ represents a hydrogen atom, a fluorine atom, a methyl group, or a trifluoromethyl group.

* * * * *